United States Patent [19]

Ong

[11] 4,239,046

[45] Dec. 16, 1980

[54] MEDICAL ELECTRODE

[76] Inventor: Lincoln T. Ong, 5940 Fairwood Dr., Minnetonka, Minn. 55343

[21] Appl. No.: 944,622

[22] Filed: Sep. 21, 1978

[51] Int. Cl.³ .............................................. A61B 5/04
[52] U.S. Cl. .................................. 128/640; 128/798; 339/151 M
[58] Field of Search ............................... 128/639–641, 128/644, 172.1, 303.13, 783, 787, 791, 798, 802, 803, DIG. 15, 207.21; 339/151 M

[56] References Cited

U.S. PATENT DOCUMENTS

| | | | |
|---|---|---|---|
| 2,590,876 | 4/1952 | Landauer | 128/798 |
| 3,542,010 | 11/1970 | Love | 128/644 |
| 3,556,105 | 1/1971 | Shepard | 128/798 |
| 3,587,565 | 6/1971 | Tatoian | 128/640 |
| 4,050,453 | 9/1977 | Castillo et al. | 128/640 |
| 4,072,145 | 2/1978 | Silva | 128/644 |
| 4,125,110 | 11/1978 | Hymes | 128/641 |

FOREIGN PATENT DOCUMENTS 311644 10/1971 U.S.S.R. ..................................... 128/798

Primary Examiner—Lee S. Cohen
Attorney, Agent, or Firm—Paul & Paul

[57] ABSTRACT

A medical electrode for stimulation iontophoresis monitoring and grounding electrical contact application to the skin surface of humans and animals may be provided having an electrically conductive substrate for interfacing with the skin, an electrically conductive stranded material may be secured to one side of the substrate and an electrically conductive knitted filament material sewn to the stranded material; preferably, a hooked connector is utilized for making an electrical connection with the knitted filament material, this connector being attachable and detachable by means of the coaction of its hooks and knitted filaments.

13 Claims, 4 Drawing Figures

MEDICAL ELECTRODE

BACKGROUND OF THE INVENTION

The subject invention relates to medical electrodes, and more specifically, to such electrodes which are used in combination with stimulation iontophoresis, monitoring, or grounding equipment. As such, these electrodes are intended to provide an electrical connection to the skin when attached to the skin surface of humans and animals.

Prior skin interface electrodes, typically, have comprised a skin interfacing member such as a gum pad, gel saturated sponge, gel layer or adhesive layer, wherein, in each instance, this interface member has been electrically conductive. A current distribution or collecting member had formed a backer to the interface member. Typically, this backer member was constructed of a metallic sheet of material or a carbon impregnated sheet of material, or the like, the distribution and collecting backer member being also electrically conductive. A snap connector was attached to this distribution and collecting member and had been used to establish an electrical connection with the distribution and collecting backer member. A female snap mating part was engaged complete an electrical circuit to a remote piece of equipment.

As alternative to the snap connector, the electrical connection has been completed to the distribution and collecting backer member by soldering or welding a section of electrical wire to that member, this electrical wire having a banana plug connector on its free end.

In some instances, a diffusion screen was utilized and positioned within an interfacing pad when this pad was of greater thickness. Typically, such a diffusion screen was positioned midway through the pad, and while not a necessary part of the electrode, it acted to further equally distribute current densities throughout the pad which resulted in more uniform current densities at the skin contact surface.

Electrical connection to the electrodes involved either the snap connector or the solder or weld joint with a disparate banana plug or other connecting pins or sockets. In the first instance, the snap connector was mated to the electrically conductive backing material (distribution and collecting member) and became permanently affixed thereto. This snap connector provided a very high profile and a sharp pressure point wherein individual electrodes may not be stacked upon one another in storage without protection of adjacent electrodes from the piercing by the adjacent snap connector. This protruding snap connector also represented a hazard to the patient if he should roll on it.

In order to provide an efficient and effective electrical connection, the ball or head of the mating portion of the snap connector must fit tightly with its mating member. As such, relatively large stresses are placed upon the backing member to which the snap connector is attached when the snap connection is made or broken. This results, very often, in a ripping of the backing material and a dislodgement of the snap connector.

The electrode configuration using the soldered or welded wire end, on the other hand, provides a concentrated stress point which often results with a broken solder joint or weld joint or a broken wire at the solder or weld point. Likewise, very often the weld point is pulled apart by the stresses exerted on the wire during everyday use, the backing material very often being quite thin and possessing little mechanical strength.

An object of this invention is to provide an electrode structure which has a very low profile and presents no sharp protrusions.

A second object of this invention is to provide such an electrode utilizing a gum interface substrate and also a backer structure which is quite pliable, this backer structure having a stranded or filament configuration which quite easily conforms to any configuration to which the gum substrate is shaped.

A further object of this invention is to provide such an electrode wherein the electrically conductive backer material which distributes or collects electrical signals across the entire surface of the gum interface substrate is of an open-weave mesh or screenlike material, this material adhering to a surface area of the substrate.

An additional object of this invention is to provide such an electrode wherein an additional material is sewn to the open-weave backer, this material providing a large area connection surface for the mating of a connector apparatus.

An even further object of this invention is to provide such an electrode wherein the large area connection surface includes a looped pile material and the mating connector includes pile loops interlocking hooks.

SUMMARY OF THE INVENTION

The objectives of this invention may be realized in a medical electrode, suitable for stimulation and monitoring application, having an electrically conductive substrate capable of being connected to an external electromedical apparatus. This substrate may be of a pliable sheet of material, preferably also having adhesive properties, and is intended to interface, on one side thereof, the surface of the skin.

A piece of electrically conductive open-weave mesh material approximating the conformation of a screen and cut to the outline and size of the interface sheet, may be adhered to the side of this substrate sheet opposite the skin interface.

A piece of electrically conductive knit material being smooth on one side and a closed looped pile material on the other side may be positioned at approximately the center of the open weave material and may be sewn or stitched thereto.

A conductive connector having projecting hooks interlockably matable with the pile side of the knit material may be utilized to provide an electrical pathway to the knit material. This connector may include an electrically conductive backer to which an electric wire may be connected and through which a plurality of projecting hooks may be interstranded. The hooked connector and pile material mechanical interlocking structure may be of the Velcro ® type.

DESCRIPTION OF THE DRAWINGS

The novel features of this invention as well as the operation and construction of the invention itself will best be understood from the following description read in connection with the accompanying drawings in which like characters refer to like parts, and in which.

DETAILED DESCRIPTION OF THE INVENTION

Medical electrodes are intended for use as efficient and effective transmission mediums between a patient's skin and electrical apparatus. The electrode invention at hand is intended to include adhesive properties sufficient to adhere to a patient's skin and to provide a skin interfacing substrate and backer structure conformable to the curvature of the skin surface to which it is applied. The electrode has a backer structure which is of a low profile, without pressure concentrating projecting surfaces. Additionally, the electrode is intended to provide a detachable electrical connection which will not concentrate stresses in the electrode structure to cause a physical breakdown thereof.

Figure 1:
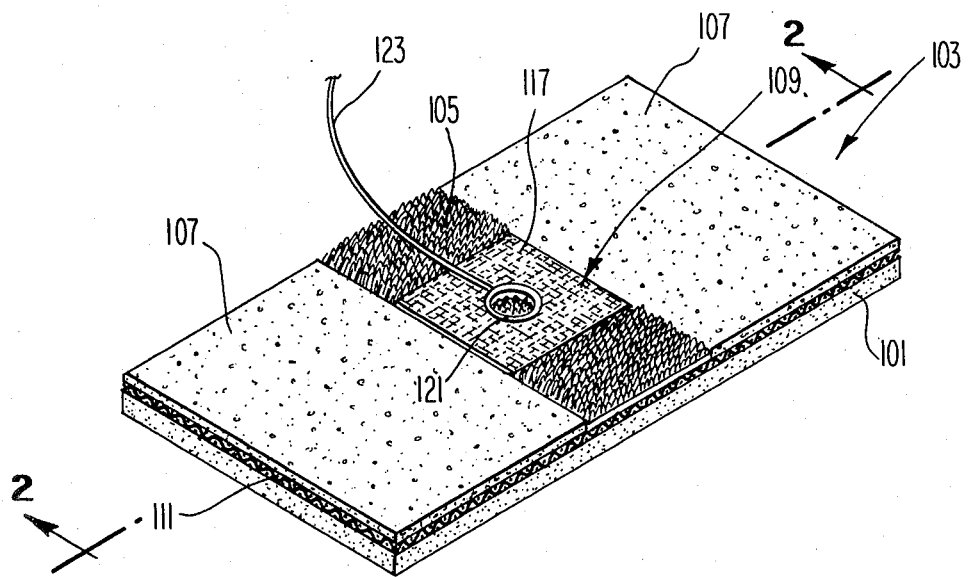
FIG. 1 shows a perspective view of the electrode.

Such an electrode can have, FIG. 1, an electrically conductive and adhesive substrage 101. Such substrate 101 can be made of electrically conductive and adhesive material as disclosed by Berg, U.S. Pat. No. 4,066,078; or of an open cellular foam saturated with electrically conductive gel, as commonly used in the industry; or of a carbon particle or silver/silver-oxide particle bearing material including an adhesive coating applied thereto as also commonly used in the industry. This substrate material 101 can be cut from sheets of varying thicknesses into any of a plurality of possible shapes. In the principle embodiment of this invention, this substrate 101 is rectangularly shaped.

An electrical backer structure 103 is attached to one side of the substrate 101. A portion of this backer 103 includes a piece of closed loop knit material 105, having a smooth underside, and which is electrically conductive. Also included are one or more sections 107 of non-conductive material. A low profile Velcro ®-type connection member 109 is used in connection with the electrically conductive loop material 105.

Figure 2:
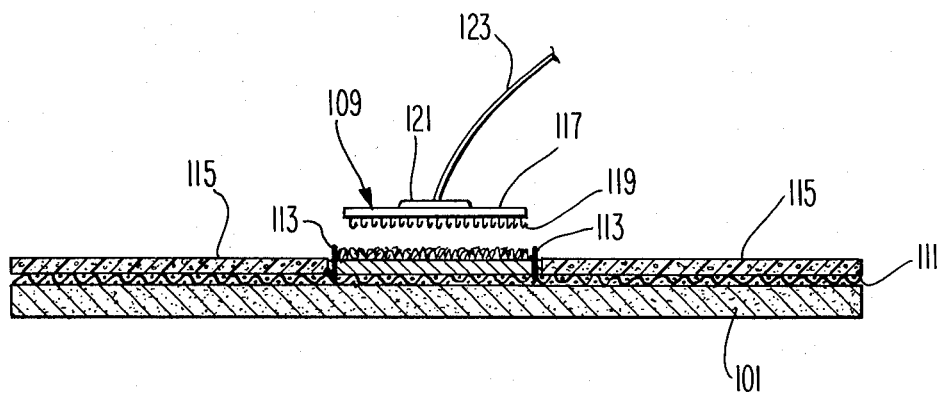
FIG. 2 shows a cross section in side elevation through the electrode of FIG. 1.
Figure 3:
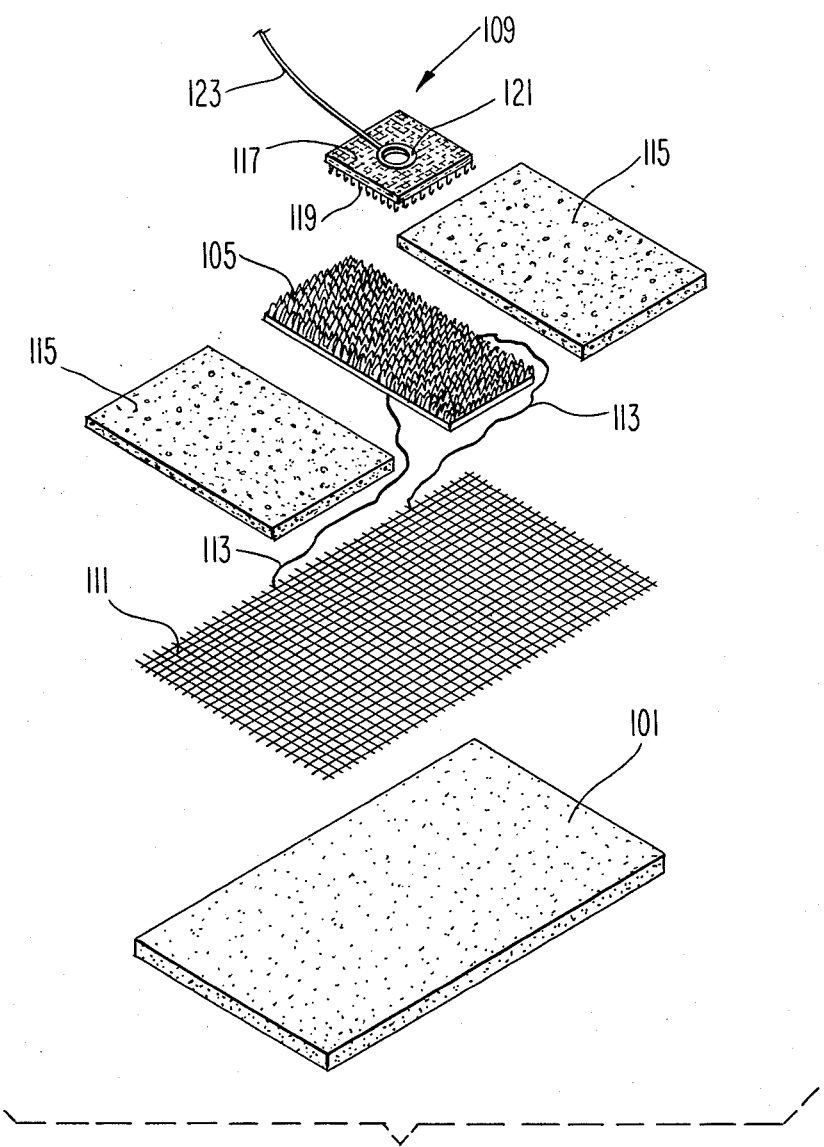
FIG. 3 shows an exploded view in perspective of the electrode showing each major element thereof.

Referring to FIGS. 2 and 3, it is readily seen how the electrode is constructed. The skin interface substrate sheet 101 being a rectangular sheet of electrically conductive and adhesive material, either self adhesive or with adhesiveness added, also possesses pliable cohesive properties which enable it to easily conform to the surface configuration of the skin to which it is applied.

Positioned on the top surface of this substrate 101, i.e., opposite the skin side, is a layer of heavy marquisette or mesh material 111 having an open-weave design which approximates a screen. This material typically can be made of 100% nylon strands, type 6-6, 40 denier, 13 filaments per end and can have a thickness of approximately 0.025 inches. This open-weave material, has its interwoven strands coated with electrically conductive material such as graphite, carbon, silver, silver oxide, aluminum powder, or gold. A resultant surface resistance less than 10 ohms per square inch, a tensil strength in excess of 125 pounds per square inch and a tear strength in excess of 10 pounds per square inch is obtained. This material may be obtained from Tecknit ® Corporation, Cranford, N.J.

The rectangular piece of knit pile material 105 is cut to size to fit neatly in the center portion of the open-weave material 111. This conductive pile material contains interwoven Velcro ®-type closed loops woven onto a backer material. Both the loops and the backer material are principally of nylon and are coated with a conductive coating of either graphite, carbon, silver, silver oxide, aluminum powder or gold. This pile material 105 is sewn onto the open weave material with its pile side facing outwardly, on at least two sides using at least two strands of ordinary cotton sewing thread 113. While this pile material 105 may be sewn onto the open-weave material 111 with more strands of thread, it has been found that two strands provide the minimum mechanical bonding needed between the backer portion of the pile material 105 and the open-weave material 111 enabling an electrical connection therebetween. This pile material, typically, has a thickness of about 1/16 inch.

Two rectangular sections of foam material 115 may be positioned on either side of the conductive pile material 105. This foam 115 is non-conductive and may be of a contrasting color as the center pile material 105. For ease of recognition, these foam sections 115 are of a slightly different shade of color from the center pile portion 105. The foam sections 115 are cut to size to completely cover the remaining uncovered portion of the open-weave material 111 and have an adhesive coating on one side thereof for adhering to the open weave material 111. These sections 115 are non-conductive being made of rubber or plastic foam and are of a similar thickness as the pile material to provide a finished uniform backer appearance.

The hooked connector 109 includes a rectangular section of nylon backer material 117 interwoven with rows of fine hooks 119. This backer material can be of nylon and the hooks can be formed of fine steel spring wire. Such hooks have been sold commercially by Velcro U.S.A. as Velcro ® hooks. Both the backer material and the hooks are coated with a conductive surface of graphite, carbon, silver, silver oxide, aluminum powder or gold. The approximate thickness of the hook material is approximately ⅛ inches. As alternative to the spring steel wire, nylon or plastic hooks having a conductive coating may be used.

A grommet or eyelet 121 having a center circular opening is fastened to the hook backer material 117 through a hole established therethrough. This eyelet can be made of brass with two portions, one of which forms a flange which is compressed to interlock with the other portion. Wound around this flange before it is compressed into its mating position, is an end of an electrical conductor wire 123. This wire 123 can be of a type readily available on the marketplace having a teflon-coated insulator covering. This covering is stripped from the wire at the eyelet mating end thereof so that the bare wire is available for wrapping around the eyelet before it is crimped into place.

The hook connector 109 mates with the conductive pile material 105 in traditional Velcro ® fashion. Closure characteristics typical of Velcro ® closures are exhibited. These closure characteristics include a shear strength of greater than 5 psi, a tensil strength of at least 4 psi and a peel effect resistive strength of at least 0.4 psi.

This unique structure provides an electrode with enhanced handling features and an electrode which may be manufactured very quickly and very simply. With the Velcro ® closure intact, i.e., the conductive hook mated with the conductive pile material, a very flat profile is exhibited by the electrode. The entire backer material being no thicker than approximately 1/16 to 3/32 inches. The entire package provides no protruding sharp edges as with the snap connector. Nor does it provide a concentrated shear point or tensil point as with a welded or soldered wire connection. The electrode may be packaged in flat plastic packs which may be stacked in heavy stacks without the fear of damage to adjacent electrodes. Moreover, with this very low profile structure, the electrode may be applied to the body without the fear of damage to adjacent electrodes. Moreover, with this very low profile structure, the electrode may be applied to the body without the fear of jabbing or injuring the patient if the patient should roll over or strike the electrode. This electrode presents an entirely pliable structure, every component portion thereof being very pliable.

The sewing of the conductive pile rectangular material 105 to the open mesh material 111 provides an easy manner of construction requiring no special tool and dye or stamp equipment and no special weld or solder equipment. The open mesh material easily adheres to the adhesive substrate 101. The foam pads 115, while they, in the principle embodiment have an adhesive coating on one side for adhering to the open mesh material 111, could in the alternative be without this adhesive coating and be sewn to the open mesh material much as is the pile material 105.

Additionally, the pile material 105 could be cut to a very large size of the same size and dimensions as the open mesh material 111. This would eliminate the necessity of having the foam backing sections 115 altogether and would allow the hook connector 109 to be attached anywhere on the outward side of the electrode as opposed to the center conductive portion as with the principle embodiment.

Instead of making the knit material 105 and the open-weave material 111 of nylon, these elements could be made of cotton, paper or any number of other natural or synthetic materials possessing the proper strength characteristics and being capable of accepting a conductive coating.

As stated above, the conductive substrate 101 may be cut to any shape. Most commonly it will be cut in circular and rectangular shapes with a thickness of approximately 3/16 inch. The open mesh material 111 is similarly cut to fit the shape of the substrate 101. The conductive pile material 105, however, need not be cut to conform with the shape of the open-weave material 111. As long as it does not overlap the open-weave material 111, it may be sewn on or glued using conductive glues at any location of this mesh 111.

The principle function of the conductive pile material 105 is to provide an electrical connection with the open mesh 111 and to provide a sufficient surface area for the interlocking hooked connector 109 to attach. It is advantageous to provide the pile material 105 with a surface area 2 to 4 times greater than the hooked connector 109.

Figure 4:
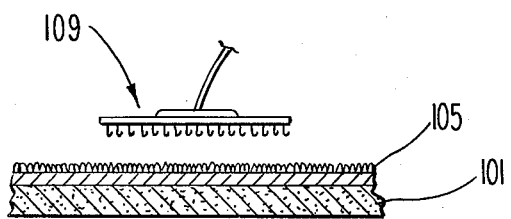
FIG. 4 shows a side elevation of an alternate embodiment of the electrode.

As an alternative, the electrode may be embodied in a configuration as shown in FIG. 4, in side elevation. In this embodiment the foam sections 115 and open weave material 111 are eliminated. A piece of closed loop knit material 105 is cut to the approximate size of the substrate 101 and is positioned directly onto the back side, i.e., one side of this substrate. The connection member 109 may with this embodiment be positioned anywhere on the backer as the closed loop knit material 105 forms the entire backer.

While the open weave mesh material 111 may be adhered to the substrate 105 by the adhesive qualities of the substrate 101, there is also a slight "flow" and mechanical interlocking of substrate 101 and open weave mesh material 111 when a soft or pliable substrate 101 material is used.

When as shown in the embodiment of FIG. 4, the closed loop knit material 105 is in direct contact with the substrate 101, this "flow" and mechanical interlocking action is minimized. However, the smooth back surface of the knit material 105 which is placed in direct contact with the surface of the substrate 101 provides a much larger surface area for adhesive bonding than with the embodiment where the open weave material 111 is in direct contact with the substrate 101. Sufficient bonding is obtained with either embodiment to withstand the pull off forces exerted by the hooks 119 of the connection member 109.

The foregoing disclosure is intended to be taken in the illustrative and not in the limiting sense. It being realized that the design of this electrode may be altered in one fashion or another without departing from the intent and scope of the invention.

What is claimed:

1. An electrode comprising:
a substrate having electrically conductive and adhesive properties;
a piece of electrically conductive stranded material adhesively adhered to by one side of said adhesive substrate and being in electrical connection therewith; and
a piece of electrically conductive knitted filament material, said knitted material being sewn to said stranded material to make an electrical connection therewith.

2. The electrode of claim 1 also comprising:
a Velcro ®-type hooked connector, said hooked connector having electrically conductive hooks protruding from a first side therof and having an electrically conductive other side with a conductor lead wire extending therefrom, said hooks being mated with said electrically conductive knitted filament material for completing the electrical connection between said lead wire and said substrate, said hooked connector being attachable and detachable by coaction of said protruding hooks and said knitted filament material.

3. The electrode of claim 2 wherein said stranded material includes a piece of open-weave mesh material having a conductive coating; wherein said knitted material has a smooth side and a closed loop pile side, both sides having a conductive coating; and wherein said smooth side of said knitted material is sewn to said open-weave mesh material with thread.

4. The electrode of claim 3 wherein said thread is nonconductive.

5. The electrode of claim 4 wherein said open-weave mesh material and said knitted material are each made of nylon and said thread is made of cotton.

6. The electrode of claim 5 wherein said Velcro ®-type hooked connector includes:
a sheet of woven electrically conductive backer material forming said electrically conductive other side;
a plurality of small hooks projecting from one side of said backer material, said hooks being electrically conductive and mechanically interlocked with said backer material weave, and being said electrically conductive protruding hooks from said first side;
an eyelet secured through said backer material, said eyelet being swaged together of two electrically conductive members being crimped one upon another; and wherein said conductor lead wire is electrically conductive and has a section wound around one of said eyelet members and being held fast thereto by said crimp.

7. The electrode of claim 6 also including at least one foam pad section, said section having at least one side covered with adhesive and adhered to an otherwise exposed portion of said open-weave mesh material.

8. The electrode of claim 7 wherein said connector backer material and said connector plurality of hooks are coated with an electrically conductive substance.

9. The electrode of claim 8 wherein said electrically conductive substance includes carbon.

10. The electrode of claim 8 wherein said electrically conductive substance includes silver.

11. The electrode of claim 8 wherein said electrically conductive substance includes gold.

12. An electrode comprising:
a substrate sheet having electrically conductive and adhesive properties; and
a piece of electrically conductive knitted material, said knitted material having a smooth side and a closed loop pile side both of which are electrically conductive, said knitted material being of the approximate shape and size of said substrate sheet and being adhered to by one side of said substrate sheet on said knitted material's smooth side.

13. The electrode of claim 12 also including an electrical connection member having a plurality of electrically conductive hooks, said hooks being mated with said knitted material closed loop pile side to make an electrical connection therewith.

* * * * *